United States Patent [19]

Fox et al.

[11] Patent Number: 4,713,324
[45] Date of Patent: Dec. 15, 1987

[54] INVERTED LATENCY SPECIFIC BINDING ASSAY

[75] Inventors: John P. Fox, Ardsley; Eddie Hedaya, Hartsdale, both of N.Y.; Violet Lippman, Teaneck, N.J.

[73] Assignee: Technicon Instruments Corporation, Tarrytown, N.Y.

[21] Appl. No.: 528,496

[22] Filed: Sep. 1, 1983

[51] Int. Cl.$^4$ .................. C12Q 1/00; G01N 33/53
[52] U.S. Cl. ........................... 435/4; 435/7;
435/8; 435/14; 435/25; 435/28; 436/520;
436/522; 436/537; 436/546; 436/829
[58] Field of Search .............. 435/7, 8, 4, 14, 25,
435/28; 436/520, 522, 546, 829, 537; 424/417, 450

[56] References Cited
U.S. PATENT DOCUMENTS

| | | | |
|---|---|---|---|
| 4,134,792 | 1/1979 | Boguslaski et al. | 436/537 |
| 4,174,384 | 11/1979 | Ullman et al. | 260/112 R |
| 4,193,983 | 3/1980 | Ullman et al. | 436/819 |
| 4,220,450 | 9/1980 | Maggio | 436/537 |
| 4,235,792 | 12/1980 | Hsia et al. | 436/817 |
| 4,342,826 | 8/1982 | Cole | 435/188 |
| 4,372,745 | 2/1983 | Mandle et al. | 436/537 |

OTHER PUBLICATIONS

Smolarsky, et al., J. Immunol. Meth., vol. 15, (1977), pp. 255-265.
Geiger, et al., J. Immunol. Meth., vol. 17, (1977).
Haga, et al., Biochem. Biophys. Res. Comm., vol. 95, (1980), pp. 187-192.
Magee, et al., J. Cell Biology, vol. 63, (1974), pp. 492-504.
Six et al., Biochemistry, vol. 13, (No. 19), pp. 4050-4058, (1974).

Primary Examiner—Robert J. Warden
Assistant Examiner—Stephen C. Wieder
Attorney, Agent, or Firm—Jeffrey M. Greenman

[57] ABSTRACT

A specific binding assay composition and method for determining a ligand in a sample are disclosed. The composition comprises (a) a binding partner for the ligand; (b) a detection system which has at least two components; (c) a selectively accessible vesicle having a surface-incorporated ligand or ligand analog and a first component of the detection system therein; (d) a substance which modifies vesicle accessibility in response to binding of surface-associated ligand or ligand analog and binding partner; and (e) at least one additional component of the detection system which is reactive with the first component to produce a detectable response which is reduced by association of the binding partner and vesicle modifying substance with the variably accessible vesicle. A decrease in signal is measured upon reaction as compared to the signal of unreacted vesicles.

22 Claims, No Drawings

INVERTED LATENCY SPECIFIC BINDING ASSAY

BACKGROUND OF THE INVENTION

1. Field of the Invention

This invention relates to the field of specific binding assays, particularly immunoassays for determining substances of clinical interest. The development of specific binding assay techniques has provided extremely useful analytical methods for determining various organic substances of diagnostic, medical, environmental and industrial importance which appear in liquid mediums at very low concentrations. Specific binding assays are based on the specific interaction between a ligand, i.e., a bindable analyte under determination, and a binding partner therefor, i.e., receptor. The presence of the receptor can be used to effect a mechanical separation of bound and unbound labeled analyte or can affect the label in such a way as to modulate the detectable signal. The former situation is normally referred to as heterogeneous and the latter as homogeneous, in that the latter technique avoids a separation step. Where one of the ligand and its binding partner is a hapten or antigen and the other is a corresponding antibody, the assay is known as an immunoassay. See, generally, Odell and Daughaday (Eds.), *Principles of Competitive Protein-Binding Assays*, J. B. Lippincott Co., Philadelphia (1971).

In conventional label conjugate specific binding assay techniques, a sample of the liquid medium to be assayed is combined with various reagent compositions. Such compositions include a label conjugate comprising a binding component incorporated with a label. The binding component in the conjugate participates with other constituents, if any, of the reagent composition and the ligand in the medium under assay to form a binding reaction system producing two species or forms of the conjugate, e.g., a bound-species (conjugate complex) and a free-species. In the bound-species, the binding component, e.g., a hapten or antigen, of the conjugate is bound by a corresponding binding partner, e.g., an antibody, whereas in the free-species, the binding component is not so bound. The relative amount or proportion of the conjugate that results in the bound-species compared to the free-species is a function of the presence (or amount) of the ligand to be detected in the test sample.

2. Brief Description of the Prior Art

Many properties of natural cell membranes can be duplicated in simple lipid bilayer systems, referred to as liposomes. One of these properties is lysis. Lysis can be achieved by conventional chemical agents, such as detergents, or by immunological reactions. When a vesicular, e.g., liposome, membrane contains an externally accessible antigen it will react with corresponding antibody, causing agglutination. When the antigen-sensitized liposome reacts with corresponding antibody in the presence of complement the membrane is irreversibly damaged and can no longer function as the intact selective permeability barrier. This is immunolysis. The extent of immunolysis has been monitored by using antigen-sensitized liposomes containing entrapped marker molecules which are released upon immunolysis.

The lysis of liposomes has been studied using a wide variety of marker systems. One type of marker system, which uses no marker-reactive reagents external to the liposome, has been disclosed in which the liposome encloses an electron paramagnetic resonance spin marker, e.g., stable free radical, such as tempocholine. Tempocholine is water soluble but membrane impermeable, therefore it can be entrapped within liposomes or vesicles and it does not leak across the lipid bilayers. Tempocholine enclosed within liposomes produces a characteristic broad paramagnetic resonance signal of small amplitude. This is because there is a high concentration of spin molecules which exchange signals due to their close proximity to one another. When the liposome membranes are ruptured, such as by activation of complement, the tempocholine molecules are released and diluted in the external medium. This results in a readily detectable, qualitative and quantitative, alteration in the paramagnetic resonance spectrum. Humphries, G. M. and McConnell, H. M. Proc. Nat. Acad. Sci. USA, 72: 2483-2487 (1975). See, also, Wei, et al., J. Immunol. Methods, 9: 165-170 (1975); Chan, et al., J. Immunol. Methods, 21: 185-195 (1978); and Hsia, et al., Ann. N.Y. Acad. Sci., 308: 139-148 (1978). Another marker system which uses no marker-reactive reagents external to the liposome employs a composition containing a fluor, such as 1-aminonaphthalene-3,6,8-trisulfonate, and a quencher, such as a,a'-dipyridinium p-xylene dibromide, entrapped within the liposome. Fluor and quencher escape upon immunolysis of the liposome and their subsequent dilution in the external volume abolishes the quenching, resulting in a high fluorescent signal. See Smolarsky, et al., J. Immunol. Methods, 15: 255-265 (1977) and Geiger, et al., J. Immunol. Methods, 17: 7-19 (1977).

Another type of marker system employs an electrode in the reaction environment external to the liposome. One example of this uses a potassium loaded liposome. Potassium ion escapes upon liposome immunolysis and reacts with an ion-selective electrode in the external environment. See Katsu, et al., Chem. Pharm. Bull, 30: 1504-1507 (1982). Tetrapentylammonium ions have also been enclosed in liposomes and detected upon immunolysis using an ion-selective electrode. See Shiba, et al., Anal. Chem., 52: 1610 (1980) and Chem. Lett. 155 (1980). Also, sheep erythrocyte ghosts (membranes) have been loaded with trimethylphenyl ammonium ion and lysis has been detected with an ion-selective electrode. D'Orazio, et al., Anal. Chem., 49: 2083 (1977) and D'Orazio, et al., Anal. Chem. Acta. 25: 109 (1979).

One of the first types of marker systems to be reported employs substrate entrapped within the liposome or erythrocyte membrane vesicle. The substrate escapes upon immunolysis of the liposome and reacts with an enzyme-containing composition in the external volume to produce a detectable response. The early examples of this use glucose entrapped within the liposome. The glucose escapes upon immunolysis and its release from the liposomes is measured by the increase in absorbance at 340 nanometers which occurs upon reduction of $NADP^+$ in the presence of hexokinase, glucose-6-phosphate dehydrogenase and the requisite cofactors. See Hixby, et al., Proc. Nat. Acad. Sci., 64: 290-295 (1969); Kinsky, et al., Biochemistry, 8: 4149-4158 (1969); Kinsky, et al., Biochemistry, 9: 1048 (1970). In a more recent example of this type of system, a fluorogenic substrate (umbelliferone phosphate) or a chromogenic substrate (p-nitrophenyl phosphate) is enclosed in the liposome. The substrate escapes upon immunolysis of the liposome and reacts with an enzyme (alkaline phosphatase) in the external volume. Free substrate is produced, resulting in an increased signal. See Six, et al., Biochemistry, 13: 4050 (1974); Uemura, et al., J. Biochem, 87: 1221 (1980); and Uemura, et al., J. Immunol. Methods, 53: 221-232 (1982).

Lysis, including immunolysis, of liposomes having internally entrapped enzymes as markers has also been reported. The enzyme reacts with substrate in the external reaction medium resulting in a detectable response. For example, experiments have been performed using trapped enzyme markers including hexokinase, glucose-6-phosphate dehydrogenase and B-galactosidase. See Kataoka, et al., Biochem. Biophys. Acta, 298: 158-179 (1973). Also, horseradish peroxidase can be entrapped within the liposome. The peroxidase escapes upon immunolysis and catalyzes the following reaction:

$$2\ NADH + O_2 + 2\ H^+ \xrightarrow{Mn^{2+}} 2\ NAD^+ + 2\ H_2O$$

Oxygen is consumed by the oxidation of NADH and resultant production of water. The depletion of oxygen is detected by an oxygen electrode. See Haga, Biochem. Biophys. Res. Comm., 95: 187-192 (1980).

Several references report the enhancement of enzymic activity upon lysis of enzyme-containing liposomes. For example, Solomon, et al., Biochem. Biophys. Acta, 455: 332-342 (1976) report this observation upon lysis of glucose oxidase-containing liposomes by either sonication or exposure to detergent. The enzymic activity of the entrapped glucose oxidase served as a measure for the permeability of the bilayer membrane of the liposomes to glucose in a non-separation assay. The oxidation of glucose was followed in the same reaction mixture before and after detergent lysis of the enzyme-containing liposome by oxygen uptake using an $O_2$ electrode. Observed enzymic activity was as high as 4.60 times greater after lysis than it was before lysis.

Tokunaga, et al., FEBS Letters, 106: 85-88 (1979) report an in vitro non-separation method for determining permeability of liposomes containing alkaline phosphatase, a-glucosidase and a-galactosidase. Enzymic activity was determined using substrate and a coupled enzyme reaction in the same reaction mixture before and after detergent lysis. Using alkaline phosphatase, observed enzymic activity was as high as 17.5 times greater after lysis than it was before lysis. These authors state that if the $K_m$ of the particular enzyme/substrate pair were the same both inside and outside of the liposome, the intravesicular enzyme activity could be related to the apparent rate of substrate permeability.

Magee, et al., J. Cell Biology, 63: 492-504 (1974) have used horseradish peroxidase-containing liposomes. The enzymic activity of horseradish peroxidase was determined spectrophotometrically in the same reaction mixture before and after detergent lysis. The ratios of the observed enzymic activity after lysis to the observed enzymic activity before lysis were as high as 8.3. They note that liposomes have been reported as useful models for membranes in permeability studies owing to their sensitivity to polyene antibiotics and susceptibility to immune lysis.

Several different homogeneous label conjugate specific binding assay systems are known in the art, one of which is disclosed by Ullman, et al., in U.S. Pat. No. 4,193,983. In this assay system, a label and a ligand or ligand analog are non-covalently bound to the external surface of a colloidal particle, such as a liposome, which is capable of maintaining its integrity in an aqueous environment. The discrete colloidal particle serves as a hub or nucleus which retains the ligand or its analog and the label in a substantially fixed average spatial relationship. By having the label and ligand in relatively close proximity on the surface of the particle, the proximity of the label and the receptor bound to the ligand adjacent the label can be used in accordance with the prior art techniques to modulate the signal from the label. Nowhere is immunolysis suggested. Indeed, the clear teaching of this reference is that lysis of the vesicle would adversely affect the spatial relationship (proximity) of label and ligand which is required for this assay procedure.

Specific binding assay systems have been proposed, using a multilayered lipid membrane vesicle which has been prepared or treated to have surface-bound ligand or ligand analog and a marker or reagent substance enclosed within the vesicle. The remaining reagents for the assay include: (1) a binding partner, e.g., antibody, for the ligand; and (2) complement to effect lysis of the vesicle upon binding of the binding partner to surface-bound ligand. Generally, see McConnell, U.S. Pat. No. 3,850,578 and McConnell, et al., U.S. Pat. No. 3,887,698 and Gregoriadis, et al., Liposomes in Biological Systems, John Wiley & Sons, N.Y. (1980), especially Chapter 12 entitled "Liposomes as Diagnostic Tools".

More particularly, immunoassay systems have been disclosed in which the use of enzyme-encapsulating liposomes is suggested. Hsia, et al., U.S. Pat. No. 4,235,792 describes a competitive homogeneous immunoassay method which employs immunolysis of an antigen-sensitized liposome containing a marker. Enzymes are among the markers disclosed (col. 6, lines 24-28).

Cole, U.S. Pat. No. 4,342,826 discloses a specific binding assay using antigen-sensitized, enzyme-containing liposomes. These liposomes are immunospecifically caused to release enzyme upon binding of corresponding antibody and fixing of active complement. Upon enzyme release, the presence or absence of enzymatic activity is detected. Cole emphasizes the advantage of providing a homogeneous system in which enzymic activity is substantially greater upon lysis, e.g., a "signal:noise" ratio of at least 5-10 and preferably above 60.

Each of the above approaches to vesicular marker systems has provided an advance of one sort or another in sequestering marker from the reaction medium and, thus, minimizing the generation of signal (latency) prior to immunolysis. That is, the signal observed from intact liposomes is considerably less than that from lysed liposomes. As demonstrated by the references, this end has been widely recognized as a major consideration in the improvement of liposome immunoassays. Further, the combined teaching of the literature in this area has been that the advantages to be achieved are enhanced when complete sequestration prior to lysis is combined with the production of a high intensity signal upon immunolysis.

SUMMARY OF THE INVENTION

In contrast to the procedures previously described and in accordance with the present invention, it has been discovered that certain marker-containing liposomes generate a high intensity signal while intact and a reduced or even extinguished signal (inverted latency) upon lysis or alteration of membrane permeability. The present invention uses the combination of a vesicle with selected reagents, such that certain reagents outside of the vesicle have access to the enclosed marker prior to any alteration of the vesicle and that alteration of the vesicle affords access by other reagents or components of the test composition. Advantages which can be achieved in accordance with the present invention include increased sensitivity, at least to the range of about $10^{-18}$ molar (M) determinations of ligand in serum samples, reduction of serum interferences, simplicity of homogeneous specific binding assay protocols, and applicability to a broader range of high and low molecular weight ligands (analytes) than previously possible for homogeneous assays.

The above advantages are achieved by a test composition for determining a ligand in a sample, which composition comprises (a) a binding partner for the ligand; (b) a detection system which has at least two components; (c) a selectively accessible vesicle having a surface incorporated ligand or ligand analog and a first component of the detection system therein; (d) a substance which modifies vesicle accessibility in response to binding of surface-associated ligand or ligand analog and binding partner; and (e) at least one additional component of the detection system which is reactive with the first component to produce a detectable response which is reduced by association of the binding partner and vesicle modifying substance with the vesicle.

Further in accordance with the present invention, there is provided a specific binding assay method for determining a ligand in a sample, which method comprises combining the test composition of the invention with a sample suspected of containing ligand and observing a change in the detectable response. Preferably, the step of combining comprises establishing a mixture of a sample suspected of containing ligand, a binding partner for said ligand, a luminescent reagent, complement and a ligand-sensitized, peroxidase-containing liposome; incubating said mixture; and combining said mixture with hydrogen peroxide. Luminescence of the mixture is observed after combination with hydrogen peroxide. The increase of intensity and duration of luminescent output is directly related to and results from the increased concentration of ligand in the sample. This increase in signal is associated with decreased availability of binding partner for binding to and initiation of complement fixation at the liposome surface. As noted above, this contrasts with signal responses previously observed where lower signal is observed with higher sample ligand concentration.

As previously stated, the liposomes of this invention exhibit higher luminescence when intact than when lysed. This phenomenon provides a basis for a useful and novel homogeneous immunoassay when such liposomes are sensitized by ligand or ligand analogue. These can interact with specific binding partners, such as antibody, to provide a composition which will undergo lysis in the presence of complement. Such lysis leads to reduced luminescence. On the other hand, ligand in the sample competes with sensitized liposome for available antibody and, to the extent that such competition occurs, complement induced lysis is reduced. Therefore, a dose-response curve can be constructed which relates increased luminescence intensity with increased concentration of ligand in the sample.

DESCRIPTION OF THE PREFERRED EMBODIMENTS

Preferred embodiments of the present invention include a luminescent specific binding assay reagent composition, a test device incorporated with one or more components of the test composition, a test kit comprised of containers or devices, each incorporated with one or more components of the test composition, in packaged combination with other components or materials, and methods of using the test composition, device and kit of the invention. Specific terms in the following description which refer only to a particular embodiment are exemplary of all of the embodiments unless otherwise indicated.

Sample fluids on which tests are performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Physiological fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated as within the meaning of this term as used and can, likewise, be assayed in accordance with the invention.

The term "ligand" refers to any substance, or class of related substances, whose presence is to be qualitatively or quantitatively determined in a sample fluid, such as those just described. The present assay can be applied to the detection of ligands for which there is a specific binding partner and, conversely, to the detection of the capacity of a liquid medium to bind a ligand (usually due to the presence of a binding partner for the ligand in the sample). The ligand usually is a peptide, protein, carbohydrate, glycoprotein, steroid, or other organic molecule for which a specific binding partner exists or can be provided by immunological or synthetic means. The ligand, in functional terms, is usually selected from antigens and antibodies thereto; haptens and antibodies thereto; and hormones, vitamins, metabolites and pharmacological agents and their receptors and binding substances. Specific examples of ligands which can be detected using the present invention are hormones such as insulin, chorionic gonadotropin, thyroxine, triidothyronine, follicle-stimulating hormone, leutinizing hormone, thyroid-stimulating hormone, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5'-adenosine monophosphate and 3',5'-guanosine monophosphate; pharmacological agents or drugs such as aminoglycoside antibiotics like gentamicin, amikacin and sisomicin, or drugs of abuse such as the opium alkaloids and ergot derivatives; antibodies such as microsomal antibody and antibodies to hepatitis and allergens; and specific binding receptors such as thyroxine binding globulin, avidin, intrinsic factor, and transcobalamin.

The terms "binding partner" or "receptor" refer to any substance, or class of substances, which has a specific binding affinity for the ligand in preference to other substances. In the majority of embodiments, the present invention will incorporate specific binding assay reagents which will interact with the ligand or its binding effectors in the sample in an immunochemical manner. That is, there will be an antigen-antibody or hapten-antibody relationship between reagents and/or the ligand or its binding effector in the sample. Such assays therefore are termed immunoassays and the special interaction between the liquid and its receptor, or binding partner, is immunochemical binding. Monoclonal antibodies are particularly suitable receptors. However, it is well understood in the art that other binding interactions between the ligand and the binding partner serve as the basis of specific binding assays, including the binding interactions between hormones, vitamins, metabolites, and pharmacological agents, and their respective receptors and binding substances. For example, polypeptide hormone receptors as binding agents or partners are discussed in Langan, et al., (Eds.), *Ligand Assay*, Masson Publishing U.S.A. Inc., New York, pages 211 et seq (1981).

The term "selectively accessible vesicle" refers to single or multi-compartmented sacs enclosing an internal volume, having a wall composed of one or more components and forming one or more internal compartments which constitute the internal volume. One example of such a vesicle is a cell ghost, formed by opening a cellular membrane, removing the internal components of the cell and resealing the membrane. Another example is a liposome, a single or multicompartmented vesicle comprised of lipids, particularly lipid mixtures including at least one phospholipid, which form a continuous wall or bilayer lipid membrane. A common constituent of these lipid mixtures is cholesterol. It has been observed that lipid mixtures containing from about 10 to 40 percent (moles cholesterol/moles total lipid) can be used to prepare liposomes useful in the composition and method of the invention. Liposomes can be prepared by any of a number of techniques. For example, multilamellar vesicles (MLVs) can be prepared by film evaporation and hydration of the lipid film. Reverse phase evaporation vesicles (REVs) may also be prepared. These are exemplary of techniques providing useful vesicles. For a general overview of liposomes and their formation, see Papahadjopoulos, et al., (Eds), Liposomes, Ann. N.Y. Acad. Sci., volume 308 (1978); Tom, et al., (Eds.), *Liposomes and Immunobiology*, Elsevier North Holland Inc., N.Y. (1980); and Gregoriadis, et al., *Liposomes in Biological Systems*, John Wiley & Sons, N.Y. (1980).

Liposomes can be made to have surface-incorporated ligand or ligand analog moieties. Such liposomes are formed using ligand-amphiphile conjugates, which usually take the form of a ligand-coupler-amphiphile molecule. Amphiphiles are substances which contain both water soluble and water insoluble regions. They are best exemplified by the lipid amphiphiles, such as the phosphatidyl ethanolamines, phosphatidyl serine, phosphatidyl inositol, sphingomyelin cerebrosides, phosphatidic acid, plasmalogens, cardiolipins and fatty acids.

In coupling the antigenic material of interest to the amphiphilic molecule, a variety of coupling reagents and coupling reactions may be employed. Thus, for example, a carboxylic acid group of an antigenic material may be coupled to an amino group of an amphiphilic molecule by direct reaction to produce an antigenic N-substituted amide wherein the N-substituent is the residue of the amphiphilic molecule. In other examples, a distinct reagent is employed to couple the antigenic material to the amphiphilic molecule and this coupling reagent may be reacted initially with either the antigenic material or with the amphiphilic molecule to produce a reactive intermediate or a precursor which can thereafter be further reacted to produce the final ligand or sensitizer conjugate. Examples of such coupling reagents include acyl isocyanates, 4-fluoro-3-nitrophenyl azides, and maleic acid and derivatives, which may be reacted with available amine groups to obtain N,N'-substituted maleimides. The fact that an antigen may first be coupled to a selected amphiphile, e.g., phosphatidyl-ethanolamine, -serine or -inositol and then included in the lipid mixture from which the liposomes are formed is most relevant inasmuch as this coupling reaction may be performed in a variety of solvents which need not necessarily be compatible with other, e.g., enzyme-containing, systems.

Alternatively, ligands may be covalently bonded or adsorbed to the surface of preformed liposomes. When liposomes are preformed, they can have at their external surface several chemical functionalities to which antigens may be covalently linked. Foremost among these are: amino groups derived from phosphatidyl-ethanolamine, hydroxyl groups provided by phosphatidyl-inositol, and carboxyl groups provided by fatty acids or phosphatidyl-serine. Thus, antigens may be coupled to preformed liposomes by traditional chemical reactions—using bifunctional coupling agents such as: glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro-m,m'-dinitrodiphenyl sulfone. Appropriate reactions which may be applied to such couplings are described in Williams et al., *Methods in Immunology and Immunochemistry* Vol. 1, Academic Press, New York (1967). In some cases, antigens may be adsorbed to the liposome surface, as was shown by Uemura and Kinsky, Biochemistry, 11: 4085–4094 (1972).

The composition of the invention further includes a substance which modifies vesicle accessibility in response to binding of surface-incorporated ligand or ligand analog and the binding partner. The principal example of this substance is a group of compounds collectively referred to as complement. Complement is one of the main humoral effectors of immune complex-induced tissue damage through cell membrane disruption or lysis. The binding of complement-fixing antibodies to ligands or ligand analogs on the surface of vesicles, such as liposomes or cell ghosts, has been shown to induce the fixation of complement. Resultant changes in membrane permeability, through actual membrane rupture or lysis or formation of functional "holes" in the otherwise intact membrane, permit the release of the detection system component(s) which had been within the vesicle or permit the access of components in the external medium to those detection components within the vesicle. The animal species from which complement is derived for use should be compatible with the source of antibody and antibody-sensitizing immunogen in accordance with known reactivities. For a general overview of complement and its effects, see Rapp, et al., *Molecular Basis of Complement Action*, Appleton-Century-Crofts (1970). Also, the role of complement is discussed in many of the references addressing other liposome immunoassays which have cited above.

The composition uses a detection system which includes at least two components. The first component is within the vesicle and at least one additional component is reactive therewith to produce a detectable response which is reduced by association of the binding partner and vesicle modifying substance with the vesicle. The principal example of this is a luminescent detection system. Luminescence is the chemical production of light. Analysis based on the measurement of emitted light offers several advantages over conventional techniques: high sensitivity, wide linear range, low cost per test, and relatively simple and inexpensive equipment. The types of luminescence that have engendered the most interest are chemiluminescence (CL) and bioluminescence (BL). The latter is the name given to a special form of luminescence found in biological systems, in which a catalytic protein increases the efficiency of the luminescent reaction. Indeed, in certain cases the reaction is impossible without a protein component. See, in general, Kricka, et al., (Eds.), *Clinical and Biochemical Luminescence*, Marcel Dekker, Inc., N.Y., NY (1982); DeLuca, et al., (Eds.), *Bioluminescence and Chemiluminescence, Basic Chemistry and Analytical Applications*, Academic Press, N.Y., NY (1981); Morawetz, et al., (Eds.), *Luminescence from Biological and Synthetic Macromolecules, Eighth Katzir Conference*, Ann. N.Y. Acad. Sci., vol. 366 (1981); and *Proceedings of International Symposium on Analytical Application of Bioluminescence and Chemiluminescence*, State Printing & Publishing, Inc., Westlake Village, CA (1979).

The process of CL in solution involves three stages: (a) preliminary reactions to provide the key intermediate; (b) an excitation step in which the chemical energy of the key intermediate is converted into electronic excitation energy; and (c) emission of light from the excited product formed in the chemical reaction. In general, the reactants include an oxidant and reductant where the reductant, as a consequence of being oxidized, emits light. Often, it is preferred to include a catalyst such as heme or peroxidase. The CL reactions described in this section all have the common feature of detecting hydrogen peroxide, an oxidant. This makes them of particular interest to the clinical chemist because they offer an alternative to the colorimetric peroxide detection methods now used in many clinical assays.

In general, hydrogen peroxide is the most commonly used oxidant. Other oxidants used include ethyl hydroperoxide, hypochlorite, iodine, permanganate, and oxygen in the presence of a suitable catalyst. Enzyme systems, including coupled enzyme systems, which produce oxidants such as hydrogen peroxide as an intermediate or end product have been used as a source of such oxidant for the luminescent detection system in accordance with the invention. Examples are the glucose/glucose oxidase or glycerol/glycerol oxidase reactions to produce hydrogen peroxide.

The phenomenon of chemiluminescence as a consequence of reaction with hydrogen peroxide has been found in several classes of reductant compounds which emit light (luminophores), particularly the cyclic diacylhydrazides. One of the most commonly used is luminol (5-amino-2,3-dihydrophthalazine-1,4-dione). A shift in the position of the amino group reduces efficiency, e.g., isoluminol (6-amino-2,3-dihydrophthalazine-1,4-dione) is 10% as efficient as luminol. Substitution in the ring structure markedly influences the luminescence. Electron-withdrawing substituents in the benzene ring decrease luminescence, but electron-donating substituents increase light yield, substitution at positions 5 and 8 being more effective than at 6 and 7. A complete loss of light occurs if the heterocyclic ring is substituted. Annelated analogs of luminol have been produced that are 300% more efficient than luminol. See, McCapra, the Chemiluminescence of Organic Compounds, Q.Rev. (London), 20: 485 (1966). Several other chemiluminescent systems have been developed including those which use lucigenins (e.g., bis-N-methylacridinium nitrate), acridinium phenyl carboxylates, diaryl oxalates such as bis(trichlorophenyl)oxalate, lophine and polyhydric phenols such as pyrogallol or gallic acid. Excellent reviews on luminescence and its role in chemical assays are provided in Gorus, et al., *Applications of Bio- and Chemiluminescence in the Clinical Laboratory*, Clin. Chem., 25: 512–519 (1979) and in Whitehead, et al., *Analytical Luminescence: Its Potential in the Clinical Laboratory*, Clin. Chem. 25: 1531–1546 (1979).

Bioluminescence (BL), as noted above, is a form of luminescence found in biological systems. In most BL systems, the enzyme luciferase catalyzes the luminescent oxidation of a substrate, luciferin. The generic term "luciferase" refers to an enzyme that catalyzes the oxidation of a substrate, such as luciferin, to produce light. The generic term "luciferin" refers to a reduced compound that can be oxidized to an electronically excited singlet state and which produces light upon its return to the ground state. The most completely studied of these systems is that of the firefly, for which the reaction is illustrated as follows:

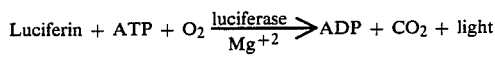

$$\text{Luciferin} + \text{ATP} + \text{O}_2 \xrightarrow[\text{Mg}^{+2}]{\text{luciferase}} \text{ADP} + \text{CO}_2 + \text{light}$$

This reaction is best carried out at about 25° C. in glycine buffer (pH 7.8). Most of the remaining BL systems have been observed in marine organisms, such as marine bacteria. For example, the reaction system in *Vibrio fischeri* and *Beneckea harveyi* is illustrated as follows:

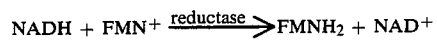

$$\text{NADH} + \text{FMN}^+ \xrightarrow{\text{reductase}} \text{FMNH}_2 + \text{NAD}^+$$

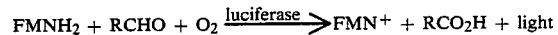

$$\text{FMNH}_2 + \text{RCHO} + \text{O}_2 \xrightarrow{\text{luciferase}} \text{FMN}^+ + \text{RCO}_2\text{H} + \text{light}$$

In this reaction RCHO is a long chain aliphatic aldehyde. The reaction is best carried out at below 25° C. in a pH range of about 6.4–7.2 for *V. fischeri* and pH 5.6–6.8 for *B. harveyi*. These and other BL systems are also fully discussed in Gorus, et al., supra and Whitehead, et al, supra.

The term "peroxidatively active substance" defines the precise chemical activity of the substances contemplated. A peroxidase is an enzyme which will catalyze a reaction wherein hydrogen peroxide oxidizes another substance. The peroxidases are generally proteins which incorporate iron porphyrin moieties. Peroxidase occurs in horseradish, potatoes, figtree sap and turnips (plant peroxidase); in milk (lacto peroxidase); and in white blood corpuscles (verdo peroxidase); also it occurs in microorganisms and may be produced by fermentation. Certain synthetic peroxidases, such as those disclosed by Theorell and Maehly in *Acta Chem. Scand.*, 4: 422–434 (1950), are also satisfactory for use in $H_2O_2$ detection systems. Less satisfactory are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides. Other substances which are not enzymes but which demonstrate peroxidative activity are: iron sulfocyanate, iron tannate, ferrous ferrocyanide, chromic salts (such as potassium chromic sulfate) absorbed on silica gel, etc.

As noted above, the luminescent detection produces light energy. It is possible to transfer this energy to another molecule(s) which produces a detectable response at a different wavelength or of a different type altogether. For example, a fluor can be added to the detection system. The luminophore and fluor can be selected such that light is emitted at the excitition wavelength of the fluor. Fluorescence is then detected at the wavelength dictated by the fluor selected. This and other energy transfer mechanisms can be combined with the luminescent system to modify the detectable signal as desired. One advantage of energy transfer systems is to overcome or avoid the interference of endogenous or background emissions of the sample under assay which are not readily distinguishable from the signal produced by the luminescent system.

Also, various inhibitors, quenchers or modulators can be included to modify the reactivity or signal of the detection system. Substances which inhibit or diminish enzyme activity are known and can be incorporated to affect the enzyme upon its release from the liposome or to penetrate this liposome upon modification of the permeability. For example, cyanide ions have been observed to reduce the activity of released peroxidase without otherwise affecting the assay system. Also, antibodies have been described which inhibit peroxidase activity. Substances which quench luminescent or fluorescent signals can be incorporated to enhance the inverted latency phenomenon observed. Several such quenching substances and mechanisms are known. For example, the above-described luminescence/fluorescence energy transfer can be accomplished using a fluorescer whose fluorescence is quenched when antigen-/antibody binding has occurred. This has been described with respective to conventional binding assay systems in *J. Clin. Path.*, 30: 526 (1977). Enzyme modulator systems have been described in Boguslaski, et al., U.S. Pat. No. 4,134,792.

The method of assay in accordance with the invention normally involves the combination of ligand-containing sample, antibody specific for the ligand sensitized, peroxidase-containing liposome and complement. After a suitable incubation period the above mixture is combined with the luminescent compound and hydrogen peroxide as the oxidant. The luminescence thereby generated is determined with a light sensitive detector such as a photomultiplier tube, photographic film or semiconductive diode.

The following working examples describe experiments which were performed in developing the present invention. Standard commercially available reagent grade chemicals were used whenever possible.

EXAMPLE I

Inverse Latency of Luminescent Liposome Systems

The experiments reported by this example demonstrate the change in luminescence of a reaction mixture comprising a horseradish peroxidase-containing liposome (HRP/liposome), a chemiluminescent (CL) compound and an oxidizing agent for the CL compound when the mixture is exposed to a detergent which lyses the liposomes. A most unexpected phenomenon was observed as described below.

Horseradish peroxidase-containing liposomes were prepared as follows. A lipid film was formed by evaporation of a mixture of 13 milligrams (mg) egg lecithin (Sigma Chemical Co., St. Louis, MO); 3 mg dicetyl phosphate (Sigma Chemical Co., supra); and 1.1 mg cholesterol in 12 ml of 4:1 chloroform/methanol, volume to volume (v/v), on the inside surface of a pear shaped flask. Evaporation was conducted under vacuum by water aspiration at 40° Centigrade (C.) until a dry film was observed. Thereafter, this film was further dried for two hours under vacuum at 0.5 mm mercury. The lipid film so formed was hydrated with 4.0 ml of TRIS buffer containing 2.0 mg horseradish peroxidase (HRP) (Miles Laboratories, Inc., Elkhart, IN) in each ml of TRIS buffer overnight at 4° C. with stirring by a magnetic bar. The tris (hydroxymethyl) aminomethane (TRIS) buffer stock solution (TRIS buffer) was made by combining 100 ml of a TRIS solution (60.5 g/l; pH 8.6) with 150 ml of an NaCl solution (58.5 g/l) and adjusting the volume to 1.0 liter with distilled water to give final concentrations of 0.05 molar (M) TRIS and 0.15M NaCL. The liposomes so formed were separated from free peroxidase by gel exclusion chromatography of a 1.0 ml volume of the lipid suspension on a 1.5×32 centimeter (cm) column of Sepharose 6B (Pharmacia Fine Chemicals, Piscataway, NJ) using TRIS buffer as the eluent. Forty effluent fractions of 1.8 ml were collected. HRP/liposomes were isolated in fractions 11–14 as confirmed by the presence of an absorbance peak (due to turbidity) at 410 nm using a Gilford Model 250 spectrophotometer (Gilford Instruments, Inc. Oberlin, OH). Fractions 12 and 13 were combined and stored under a nitrogen atmosphere at 4° C.

Luminol reagent solution was prepared as follows. A 221.5 mg portion of luminol (Aldrich Chemical Co., Milwaukee, WI) was dissolved in 50 ml of TRIS buffer, to which 4 drops of 50% NaOH (w/v) were added to completely dissolve the luminol, producing a $2.5 \times 10^{-2}$M luminol solution. A 0.5 ml volume of this solution was mixed with 49.5 ml TRIS buffer to provide the luminol reagent solution having a $2.5 \times 10^{-4}$M luminol concentration.

The $H_2O_3$ reagent was made by adding 14 μl of 30% (v/v aqueous $H_2O_2$ (Fisher Scientific, Orangeburg, NY) to 50 ml TRIS buffer.

The combined HRP/liposome fraction (fractions 12 and 13) was assayed by catalytic oxidation of luminol in the presence of $H_2O_2$ as follows. A 1.0 ml volume of each of a series of dilutions of HRP/liposomes was prepared in TRIS buffer. An equivalent series of dilutions was prepared in TRIS buffer containing 1% (w/v) TRITON-X-100 (Rohm & Haas Co., Philadelphia, PA). A 100 μl volume of each dilution was injected into a separate polypropylene tube which was positioned in a Turner Model 20 Luminometer (Turner Designs, Mountain View, CA) and which contained 200 μl of $2.5 \times 10^{-4}$M luminol and 200 μl of $2.5 \times 10^{-3}$M $H_2O_2$ in TRIS buffer. After the reaction was thus initiated in the particular reaction mixture being assayed, luminescence was monitored in each by integration of the signal for 60 seconds after a 0.5 second delay and recorded as arbitrary luminescence units. The observed integrated luminescence for HRP/liposomes chemically lysed with TRITON-X-100 and for intact HRP/liposomes, as well as the ratio of the signal from lysed and intact HRP/liposomes (L/I) for each of the liposome dilutions are set forth in Table I.

TABLE I

| HRP/liposomes (dilutions) | CL Response (with Triton) | CL Response (no Triton) | L/I Ratio |
|---|---|---|---|
| 1/5 | 140 | 670 | 0.21 |
| 1/10 | 18.8 | 324 | 0.06 |

TABLE I-continued

| HRP/liposomes (dilutions) | CL Response (with Triton) | CL Response (no Triton) | L/I Ratio |
| --- | --- | --- | --- |
| 1/50 | 1.5 | 64 | 0.02 |
| 1/100 | 0.7 | 30 | 0.02 |
| 1/500 | 0.24 | 6.2 | 0.04 |
| 0 | 0.19 | 0.29 | 0.66 |

The data in Table I document an unexpected phenomenon. The luminescence observed for intact liposomes is greater than that for chemically lysed liposomes. This represents an inverse latency in that the luminescent response of lysed liposomes divided by the luminescent response of intact liposomes is less than 1.0. This observation represents the basis for construction of a specific binding assay for which the luminescence derived from intact liposomes is greater than the luminescence derived from liposomes which are lysed by antibody and complement, as demonstrated in later Examples.

EXAMPLE II

The next experiments which were performed investigated whether the greater luminescence of intact liposomes over the "quenched" luminescence of chemically lysed liposomes, as observed and reported in Example I, was caused by exposure and potential inactivation of free peroxidase by the lysis agent, e.g., TRITON-X-100 detergent.

To begin, solutions of HRP were prepared by adding 2.0 mg of HRP to a 5.0 ml aliquot of TRIS buffer giving a concentration of $1 \times 10^{-5}$M HRP, as determined by the absorbence at 403 nm using an extinction coefficient of 91 mM$^{-1}$ cm$^{-1}$. A series of dilutions of this HRP solution was prepared in TRIS buffer. An equivalent series of dilutions was prepared in TRIS buffer containing 1% (w/v) TRITON-X-100. A 100 μl volume from each of these solutions was injected into separate 8×50 millimeter (mm) polypropylene tubes which were positioned in a Turner Model 20 luminometer and which contained 200 μl of $2.5 \times 10^{-4}$M luminol and 200 μl of $2.5 \times 10^{-3}$M $H_2O_2$ in TRIS buffer. After the reaction was thus initiated in the particular reaction mixture being assayed, luminescence was monitored in each by integration of the signal for 60 seconds after a 0.5 second delay and recorded. The observed integrated chemiluminescence for HRP solutions with and without TRITON-X-100, as well as the ratio for each of the dilutions is set forth in Table II.

TABLE II

| [HRP] M | CL Response (with TRITON) | CL Response (no TRITON) | Ratio |
| --- | --- | --- | --- |
| $2 \times 10^{-7}$ | 1886 | 1598 | 1.18 |
| $5 \times 10^{-8}$ | 355 | 295 | 1.20 |
| $4 \times 10^{-8}$ | 247 | 202 | 1.22 |
| $2.5 \times 10^{-8}$ | 126 | 101 | 1.25 |
| 0 | 0.1 | 0.1 | 1.00 |

Enhancement of peroxidase catalyzed oxidation of luminol by $H_2O_2$ was observed in the presence of TRITON-X-100. Thus, TRITON-X-100 does not inhibit peroxidase catalyzed oxidation of luminol and is not the cause of the quenching phenomenon reported in the previous Example.

EXAMPLE III

The next experiments which were performed investigated the effect of empty liposomes on the chemiluminescent signal observed in a free peroxidase-catalyzed oxidation of luminol by $H_2O_2$. This was done to determine whether the inverted latency phenomenon would result from the combined presence of free peroxidase and empty liposomes.

Liposomes were prepared as follows. First, a lipid film was formed by evaporation of a mixture of 7.3 mg egg lecithin, 1.75 mg dicetyl phosphate and 2.9 mg cholesterol in 13 ml of 4:1 $CHCl_3$/methanol (v/v) to dryness on the inside surface of a 50 ml pear-shaped flask. Evaporation was conducted under vacuum as described in Example I. The lipid film so formed was hydrated with 2.0 ml of TRIS buffer, to which no peroxidase had been added, overnight at 4° C. with stirring by a magnetic stirring bar and the liposome preparation so formed was maintained by storage at 4° C. for use in the manner described below.

An HRP solution was prepared by adding 13.6 mg of HRP to 5.0 ml of TRIS buffer giving a concentration of $5 \times 10^{-5}$M HRP, as determined by the absorbance at 403 nm using an extinction coefficient of 91 mM$^{-1}$ cm$^{-1}$. This solution was then diluted to a concentration of $5 \times 10^{-7}$M by combining 0.25 ml with 25 ml TRIS buffer to make a solution which was used to prepare samples with (1) enzyme only, (2) enzyme plus TRITON-X-100, (3) enzyme plus empty liposomes, and (4) enzyme plus TRITON and empty liposomes. The formulation of each of the above mixtures and controls (minus HRP) is set forth in Table III. A 100 μl volume of each of these solutions was injected into separate polypropylene tubes which contained 200 μl of $2.5 \times 10^{-4}$M luminol and 200 μl of $2.5 \times 10^{-3}$M $H_2O_2$ in TRIS buffer and were positioned in a Turner Model 20 Luminometer. After the reaction was thus initiated in the particular reaction mixture being assayed, luminescence was monitored by integration of the signal for 60 seconds after a 0.5 second delay and recorded. The CL response was observed in each tube in the same manner as described in Example I and is also set forth in Table III.

TABLE III

| | HRP (μl) | TRIS Buffer (μl) | 1% TRITON (μl) | Liposomes (μl) | CL Response |
| --- | --- | --- | --- | --- | --- |
| (a) | 0 | 1000 | 0 | 0 | 2.7 |
| (b) | 0 | 300 | 700 | 0 | 1.9 |
| (c) | 0 | 800 | 0 | 200 | 0.8 |
| (d) | 0 | 100 | 700 | 200 | 0.6 |
| (e) | 50 | 950 | 0 | 0 | 5.1 |
| (f) | 50 | 250 | 700 | 0 | 4.2 |
| (g) | 50 | 750 | 0 | 200 | 2.0 |
| (h) | 50 | 50 | 700 | 200 | 2.6 |
| (i) | 100 | 900 | 0 | 0 | 11.3 |
| (j) | 100 | 200 | 700 | 0 | 12.3 |
| (k) | 100 | 700 | 0 | 200 | 5.1 |
| (l) | 100 | 0 | 700 | 200 | 7.2 |

The data in Table III first shows that only very slight luminescence is observed in preparations (a)–(d) which contained no HRP, particularly in preparations (c) and (d) which included empty liposomes. Preparations (e)–(f) show high level luminescence in the presence of 50 μl HRP. In contrast, preparations (g) and (h) contained 50 μl HRP and empty liposomes in the absence and presence, respectively, of TRITON-X-100 and displayed a luminescence which was only half that seen in the absence of liposomes. A comparison of preparations (g) and (h) shows that TRITON-X-100 has the effect of slightly increasing luminescence in the presence of liposomes. Preparations (i) and (j) show high level luminescence in the presence of 100 μl HRP. In contrast, preparations (k) and (l) contained 100 μl HRP and empty liposomes in the absence and presence, respectively, of TRITON-X-100 and displayed substantially less luminescence. A comparison of preparations (k) and (l) shows that TRITON-X-100 had the effect of slightly increasing luminescence in the presence of liposomes. In summary, addition of empty liposomes to horseradish peroxidase external to the liposome resulted in decreasing the luminescent signal. When TRITON-X-100 was included in the incubation mixture the chemiluminescent signal was enhanced.

EXAMPLE IV

Luminescent Liposome Theophylline Assay

Theophylline (1,3-dimethylxanthine) is commonly used in the treatment of bronchial asthma. The serum concentration of the drug must be closely monitored since the drug has a narrow therapeutic range of 10–20 μg/ml, while drug concentrations in excess of 20 μg/ml may be toxic. The experiments reported below demonstrate that the inverted latency luminescent immunoassay of the invention can be used to quantitate serum levels of theophylline.

Sensitized HRP/Liposome Preparation

Theophylline-sensitized HRP/liposomes were prepared as follows. First, a lipid film was formed by evaporation, as described in Example I, of a mixture of 7.3 mg egg lecithin, 1.7 mg dicetyl phosphate, 0.6 mg cholesterol and 0.15 mg theophylline conjugate in 10.0 ml of 4:1 chloroform/methanol (v/v) on the inside surface of a pear-shaped flask. The theophylline sensitizer used was a theophylline-dipalmitoyl phosphatidyl ethanolamine conjugate (theophylline-DPPE). Such a conjugate can be prepared by the procedure described in Haga, et al., *Biochem. Biophys. Res. Comm.*, 95: 187–192 (1980). This same theophylline-DPPE conjugate was synthesized by a modified procedure and analyzed to confirm its identity and purity. The purified conjugate was obtained as a preparative liquid chromatography isolate which showed a single spot on thin-layer chromatography. The identity of this conjugate was confirmed by NMR, UV and IR spectra and elemental analysis.

The lipid film so formed was hydrated with 2.0 ml of TRIS buffer containing 2 mg/ml HRP overnight at 4° C. with stirring by a magnetic stirring bar. The theophylline-sensitized HRP/liposomes so formed were separated from free peroxidase by chromatography of 1.0 ml of the lipid suspension on a 1.5×32 cm column of Sepharose 6B using TRIS buffer as the eluent. Forty effluent fractions of 1.8 ml were collected. Theophylline-sensitized HRP/liposomes were found in fractions 12–14 and free peroxidase in fractions 27–34.

Each of the effluent fractions so collected were assayed spectrophotometrically to confirm the presence or absence of peroxidase as follows. A 50 μl aliquot of each fraction was combined with 200 μl of TRIS buffer. Each of a parallel set of fraction aliquots was combined with 200 μl of TRIS buffer which contained 1% (w/v) TRITON-X-100. A 20 μl aliquot of each preparation was introduced into a 1.0 cm optical pathlength cuvette which contained 3.0 ml TRIS buffer and 50 μl of a stock guiacol (O-methoxyphenol; Matheson, Coleman & Bell, Norwood, OH) reagent (2.45 mg/ml TRIS buffer). Each of these cuvettes was positioned in a Gilford Model 250 spectrophotometer and the reaction was initiated by addition of 50 μl of an $H_2O_2$ stock solution, made by combining 50 μl of 30% (v/v) aqueous $H_2O_2$ solution (Fisher Scientific Co., Pittsburgh, PA) with 100 ml TRIS buffer. The contents of each cuvette were monitored at 436 nm wavelength for 60 seconds after initiation of the reaction. The results of this procedure confirmed the presence of peroxidase in fractions 12–14 and 27 to 34. Since liposomes were observed, as noted above, only in fractions 12–14, it was ascertained that fractions 27 to 34 contained free horseradish peroxidase.

Other Reagent Preparation

Theophylline samples of 1.25, 2.5, 5, 10, 20, 50 and 100 μg/ml theophylline were prepared from a stock theophylline solution, which consisted of 5.3 mg theophylline (Sigma, supra) dissolved in 50 ml TRIS buffer, by appropriate dilution of aliquots with additional TRIS buffer.

Anti-theophylline antibody reagent was prepared from a commercially available anti-theophylline rabbit antiserum (Kallestad Inc., Austin, TX, Catalog No. 334) as follows. A 100 μl volume of the Kallestad antiserum was added to 900 μl of TRIS buffer to make a 1:10 (v/v) stock antibody solution.

Complement reagent was prepared as follows. A vial containing lyophylized guinea pig serum (Pel Freeze, Rogers, AK, Catalog No. 38005-1, was reconstituted with 3.0 ml distilled water. A 0.5 ml volume of the reconstituted complement-containing serum was combined with azide-TRIS buffer to make a 1:10 (v/v) dilution, used in the assay procedure. This azide TRIS buffer was made by dissolving 208.1 mg sodium azide in 100 ml TRIS buffer.

Assay Procedure and Results

First a 10 μl volume of each of the theophylline samples described above was dispensed into one tube of two duplicate sets of test tubes. Then 50 μl of a 1:5 dilution in TRIS buffer of the stock antibody solution was introduced into each tube of the first set of tubes and 50 μl of a 1:10 dilution of stock antibody in TRIS buffer was introduced into each tube of the second set. Next, 40 μl of a 1:4 dilution in TRIS buffer of the theophylline-sensitized liposome preparation (fraction 13) was introduced into the mixture in each tube of the first set and 40 μl of a 1:10 dilution in TRIS buffer was introduced into the mixture in each tube of the second set. Both sets were then incubated at 37° C. for five minutes. After the five minute incubation period, a 100 μl volume of a 1:10 dilution in TRIS buffer of the complement reagent was introduced into the mixture in each tube of both sets. They were then incubated at 37° C. for an additional five minutes.

Controls were also prepared using 10 μl volumes of a 10, 50, 100 μg/ml theophylline sample and a blank TRIS buffer which contained no theophylline by adding 40 μl of the 1:4 dilution of the liposome preparation and 150 μl of TRIS buffer in lieu of the antibody and complement. A 100 μl aliquot of each of these preparations was withdrawn and injected into a separate polypropylene tube positioned in a Turner Model 20 Luminometer and which contained 200 μl of the $2.5\times10^{-4}$M luminol reagent and 200 μl of the $2.5\times10^{-3}$M $H_2O_2$ reagent. After the reaction was thus initiated in the particular reaction mixture being assayed, luminescent output was monitored by integration for 60 seconds after a 0.5 second delay and recorded. The results observed are set forth in Table IV.

TABLE IV

| Theophylline (ug/ml) | CL Response | | |
|---|---|---|---|
| | ⅓ dilution of liposomes | 1/10 dilution of liposomes | Control mixture |
| 0 | 157 | 55.0 | 258 |
| 1.25 | 139 | 57.5 | — |
| 2.5 | 181 | 63.6 | — |
| 5 | 186 | 98.5 | — |
| 10 | 234 | 100.1 | 268 |
| 20 | 274 | 125.5 | — |
| 50 | 272 | 126.2 | 266 |
| 100 | 256 | 114.7 | 257 |

An increase in luminescence is observed with increasing sample theophylline concentration for both reagent formulations. In contrast, the control solutions produced uniformly undiminished luminescence, regardless of sample theophylline concentration. This clearly and simply demonstrates the application of the inverted latency phenomenon to an immunoassay composition and method for the quantitative determination of theophylline levels at least as low as 1.25 µg/ml and at concentrations 5-fold that of the threshold toxic dose.

EXAMPLE V

This example demonstrates the effect of an inhibitor of peroxidase, cyanide ion, on the signal observed for intact liposomes and liposomes which were chemically lysed with TRITON-X-100 in a luminescent assay for peroxidase in which luminescence of the reaction mixture is recorded at a fixed time interval after initiation of the reaction.

Liposomes prepared in Example I were separated from free peroxidase by gel exclusion chromatography by the procedures described in Example I. Effluent liposome fractions were combined and stored as a stock suspension at 4 degrees C. A working suspension of a 1/40 dilution of the stock liposome suspension was prepared in TRIS buffer (intact liposomes). Similarly, a 1/40 dilution of the stock liposome suspension was prepared in TRIS buffer containing 0.2% (w/v) TRITON-X-100 (lysed liposomes).

A 1 mM stock solution of sodium cyanide (NaCN) in TRIS buffer (1 mM CN-TRIS) was prepared by dissolving 5.0 mg of NaCN in 100 ml of TRIS buffer. Reagent solutions of sodium cyanide in TRIS buffer were made from 1 mM CN-TRIS to contain 0.083, 0.2, 0.33, 0.5 and 0.75 mM NaCN in TRIS buffer.

Luminescence of intact and chemically lysed liposomes was measured by injection of 100 µl of the 1/40 liposome dilution into separate polypropylene tubes which contained 300 µl of either TRIS buffer or 300 µl of one of the cyanide reagent solutions, 50 µl of $5 \times 10^{-3}$M $H_2O_2$ in TRIS buffer, and 50 µl of $10^{-2}$M luminol in TRIS buffer. These tubes were positioned in a Turner Model 20 luminometer. Luminescence was recorded at 15 minutes after initiation of the reaction. Table V sets forth the observed luminescence for intact and chemically lysed liposomes, as well as the ratio of the signal from lysed and intact HRP/limposomes, (L/I ratio), for each of the concentrations of cyanide, [CN] mM, in the reagents.

TABLE V

| [CN] mM | CL RESPONSE WITH TRITON | CL RESPONSE NO TRITON | L/I RATIO |
|---|---|---|---|
| 0 | 1056 | 1388 | 0.76 |
| 0.083 | 10.9 | 927 | 0.01 |
| 0.20 | 17.3 | 913 | 0.02 |
| 0.33 | 27.0 | 963 | 0.03 |
| 0.50 | 27.9 | 997 | 0.03 |
| 0.75 | 30.1 | 1004 | 0.03 |
| 1.00 | 21.9 | 921 | 0.02 |

Under conditions of the experiment in which no cyanide was present, the L/I ratio was 0.76. At the lowest concentration cyanide reagent, 0.083 mM, the L/I ratio was 0.01. Luminescence of intact liposomes was inhibited no more than 34% by the range of cyanide concentrations tested. Luminescence of chemically lysed liposomes was inhibited more than 97% at concentrations of cyanide used in these experiments. Thus, this demonstrates that the presence of cyanide enhances the inverted latency phenomenon observed.

EXAMPLE VI

This example demonstrates an inverse latent ratio by use of an inhibitor of peroxidase, cyanide ion, under conditions such that an inverse latent ratio is not otherwise observed.

The theophylline-sensitized liposomes containing horseradish peroxidase prepared in Example IV were used in this series of experiments. A working suspension of liposomes was prepared by diluting an aliquot of fraction 13 into TRIS buffer as follows. A 12 µl aliquot of fraction 13 was added to 588 µl of TRIS buffer to make a 1/50 dilution (intact liposomes). Similarly, a 12 µl aliquot of fraction 13 was added to 588 µl of TRIS buffer containing 0.7% (w/v) TRITON-X-100 to make a 1/50 dilution (lysed liposomes).

A reagent solution of 0.33 mM sodium cyanide in TRIS buffer was prepared by addition of 2.0 mL of 1 mM CN-TRIS to 4.0 mL of TRIS buffer.

Luminol reagents were made from a stock solution of $2.5 \times 10^{-2}$M luminol in TRIS buffer prepared as described in Example I by dilution into TRIS buffer. Concentrations of luminol reagents are set forth in Table VI.

Hydrogen peroxide reagents were made as follows. A stock solution of $5 \times 10^{-2}$M $H_2O_2$ was prepared by addition of 57 µl of 30% (v/v) aqueous $H_2O_2$ to 10.0 ml of TRIS buffer. Next, this stock solution was used to prepare the hydrogen peroxide reagents by dilution with TRIS buffer to give the concentrations set forth in Table VI.

Luminescence of intact and chemically lysed liposomes was measured by injecting 100 µl of the working suspension of intact liposomes or 100 µl of the working solution of chemically lysed liposomes into separate polypropylene tubes which contained 300 µl of 0.33 mM CN-TRIS, 50 µl of one of the luminol reagents and 50 µl of one of the $H_2O_2$ reagents. The tubes were positioned in a Turner Model 20 luminometer. Luminescence was monitored for the reaction in each tube by integration of the signal for 60 seconds after a 0.5 second delay and recorded.

Luminescence was also recorded for intact and chemically lysed liposomes in a control experiment for which the cyanide reagent was replaced with TRIS buffer. The observed luminescence, concentration of luminol and hydrogen peroxide in the reagents and the ratio of the signal for lysed/intact liposomes, (L/I ratio), without cyanide is set forth in Table VI, experiment (a). Similarly the observed luminescence for experiments in which the concentration of sodium cyanide in the reaction mixture was 0.2 mM is set forth in Table VI, experiments (b)–(e).

TABLE VI

|     | $[H_2O_2]$ M | [LUMINOL] M | CL RESPONSE WITH TRITON | CL RESPONSE NO TRITON | L/I RATIO |
| --- | --- | --- | --- | --- | --- |
| (a) | $10^{-3}$ | $10^{-2}$ | 630 | 112 | 5.6 |
| (b) | $10^{-3}$ | $10^{-2}$ | 5.8 | 67 | 0.09 |
| (c) | $5 \times 10^{-2}$ | $10^{-2}$ | 6.0 | 736 | 0.008 |
| (d) | $10^{-2}$ | $10^{-2}$ | 11.0 | 456 | 0.02 |
| (e) | $10^{-2}$ | $10^{-3}$ | 3.4 | 71 | 0.05 |

The data in Table VI show that under conditions where an inverse latent ratio is not observed, experiment (a), addition of an inhibitor of peroxidase to the luminescent reaction mixture, experiment (b), results in diminution of the signal from lysed liposomes to a greater extent than for intact liposomes. The L/I ratio was 5.6 with no cyanide in the reaction mixture, experiment (a), while the L/I ratio was 0.09 in the presence of an inhibitor of peroxidase, cyanide, experiment (b). Experiments (b)–(e) show the inverted latency over a range of $H_2O_2$ and luminol concentrations.

EXAMPLE VII

This example describes the use of liposomes containing horseradish peroxidase in an immunoassay procedure for theophylline in which the luminescent signal derived from intact liposomes is greater than that of lysed liposomes. Peroxidase was assayed by oxidation of luminol with $H_2O_2$ as the oxidant. Luminescence was monitored by recording the signal at a fixed time after initiation of the reaction. An inhibitor of peroxidase, cyanide ion, was included in the luminescent reaction mixture.

Reagent Preparation

The theophylline-sensitized liposomes containing peroxidase prepared in Example IV were used for this series of experiments. A liposome suspension was prepared by dilution of fraction 13, Example IV, 1/10 with TRIS buffer (liposome reagent).

Anti-theophylline antiserum and complement were from the same source described in Example IV. Antibody reagent was prepared by dilution of anti-theophylline antiserum 1/10 with TRIS buffer (antibody reagent). Complement reagent was prepared by dilution of guinea pig serum 1/10 with TRIS buffer (complement reagent).

Theophylline samples of 2.5, 5, 10, 20, 40, 60, and 100 µg/ml were prepared from the stock theophylline solution of Example IV, by dilution with TRIS buffer.

A reagent solution of $5 \times 10^{-2}$ M $H_2O_2$ was prepared by addition of 57 µl of 30% $H_2O_2$ (v/v) to 10.0 ml of TRIS buffer ($H_2O_2$ reagent).

A reagent solution of $10^{-2}$ M luminol was prepared by dissolving 179 mg of luminol in about 80 ml of TRIS buffer to which 4 drops of 50% NaOH (w/v) were added. The pH of this solution was adjusted to 8.6 with dilute HCl and the volume adjusted to 100 ml by addition of TRIS buffer (luminol reagent).

A reagent solution of 0.33 mM NaCN in TRIS buffer, pH 8.6 was prepared as described in Example VI (cyanide reagent).

Assay Procedure and Results

In separate test tubes, 20 µl of one of the theophylline samples as described above, or 20 µl TRIS (0 µg/ml theophylline) was incubated with 50 µl of antibody reagent and 100 µl of complement reagent at 37 degrees C. for 5 minutes. Liposome reagent, 50 µl, was added to the mixture of sample, antibody and complement reagent and incubation was continued at 37 degrees C. for another 2 minutes. A 100 µl aliquot from each of these assay mixtures was withdrawn and injected into separate polypropylene tubes positioned in a Turner Model 20 luminometer. Each polypropylene tube contained 300 µl cyanide reagent, 50 µl $H_2O_2$ reagent, and 50 µl luminol reagent. Luminescence was recorded 11 minutes after initiation of the reaction in each tube.

The concentration of theophylline in each sample and the observed luminescence is set forth in Table VII.

TABLE VII

| [THEOPHYLLINE] µg/ml | LUMINESCENCE |
| --- | --- |
| 0 | 265 |
| 2.5 | 341 |
| 5 | 389 |
| 10 | 431 |
| 20 | 479 |
| 40 | 559 |
| 60 | 597 |
| 100 | 625 |

A dose response relationship between the luminescence of the mixture of sample, antibody reagent, complement reagent, liposome reagent, cyanide reagent, $H_2O_2$ reagent and luminol reagent, and the amount of theophylline in the sample is evident from the data presented in Table VII.

EXAMPLE VIII

The next series of experiments demonstrates the use of glucose oxidase and glucose and oxygen to generate $H_2O_2$ from oxygen and the use of cyanide, an inhibitor of peroxidase, in an immunoassay for theophylline-sensitized liposomes containing peroxidase.

Reagent Preparation

Theophylline solutions of 2.5, 5, 10, 20, 40, 60 and 100 µg/ml in TRIS buffer were prepared from the stock theophylline solution of Example IV. A 1.0 ml aliquot of each theophylline solution was combined with 1.0 ml of normal rabbit serum (Irvine Scientific, Irvine, CA) to obtain theophylline samples of 1.25, 2.5, 5, 10, 20, 30 and 50 µg/ml. Similarly, a 1.0 ml aliquot of TRIS buffer was combined with a 1.0 ml aliquot of normal rabbit serum to prepare a 0 µg/ml theophylline sample.

A solution of $8 \times 10^{-2}$ M luminol was prepared by dissolving 719.8 ml luminol in about 40 ml of TRIS buffer to which 8 drops of 50% NaOH (w/v) were added. The final volume was adjusted to 50 ml with TRIS buffer. This solution was filtered through a 0.45 µ Millipore filter before use. A stock solution of $4 \times 10^{-2}$ M luminol was prepared by combining 10.0 ml of $8 \times 10^{-2}$ M luminol with 10.0 ml of TRIS buffer.

A solution of 4.0 mg/ml glucose oxidase (Boehringer Mannheim, Indianapolis, IN lyophilized grade 1 from *Aspergillus niger*) was prepared by dissolving 40 mg of glucose oxidase in 10.0 ml of TRIS buffer. A 1.0 ml aliquot of this solution was combined with 9.0 ml of TRIS buffer to make a stock solution of 0.4 mg/ml glucose oxidase.

A 1/10 dilution of theophylline-sensitized liposomes was made by combining 0.25 ml of fraction 13, Example IV, with 2.25 ml of TRIS buffer.

A reagent containing luminol, glucose oxidaes, and theophylline-sensitized liposomes was prepared by combination of 2.0 ml of the $4\times10^{-2}$M stock luminol with 2.0 ml of the 1/10 liposome suspension and 4.0 ml of the 0.4 mg/ml glucose oxidase (Reagent 1).

A solution of 0.2M glucose was prepared by dissolving 1.82 grams of glucose (Aldrich, Milwaukee, WI) in 50.0 ml TRIS buffer. A stock solution of $4\times10^{-2}$M glucose, 0.8 mM NaCN in TRIS buffer was prepared by combining 0.5 ml of 0.2M glucose with 2.0 ml of the 1 mM CN-TRIS prepared in Example V.

Anti-theophylline antiserum and guinea pig serum were from the same sources described in Example IV. A 1/20 dilution of anti-theophylline antiserum was prepared by combining 0.25 ml of rabbit anti-theophylline antiserum with 4.75 ml of TRIS buffer. A 1/1.25 dilution of complement was prepared by combining 2.0 ml of guinea pig serum with 0.5 ml of TRIS buffer.

A reagent containing glucose, cyanide, anti-theophylline antiserum and complement was prepared by combining 1.0 ml of the 1/20 dilution of rabbit anti-theophylline antiserum with 1.0 ml of the 1/1.25 dilution of guinea pig serum and 2.0 ml of the stock solution of $4\times10^{-2}$M glucose and 0.8 mM NaCN in TRIS buffer (Reagent 2).

Assay Procedure and Results

A 20 μl aliquot of each of the theophyline samples in 50% (v/v) normal rabbit serum was separately combined with 200 μl of Reagent 1 in a polypropylene tube and mixed. Reactions were initiated by addition of 200 μl of Reagent 2 to the above and mixed. Each polypropylene tube was then positioned in a Turner Model 20 luminometer and the luminescence observed and recorded 15 minutes after initiation of the assay.

Table VIII sets forth the concentration of theophylline in each sample and the luminescence recorded.

TABLE VIII

| THEOPHYLLINE (μg/ml) | LUMINESCENCE |
|---|---|
| 0 | 138 |
| 1.25 | 152 |
| 2.5 | 227 |
| 5.0 | 270 |
| 10.0 | 338 |
| 20.0 | 471 |
| 30.0 | 510 |
| 50.0 | 492 |

A dose response relationship between the amount of theophylline in each sample and the recorded luminescence is evident from the data presented in Table VIII.

What is claimed is:

1. A composition for determining a ligand in a sample, which composition comprises:
   (a) a binding partner for said ligand;
   (b) a detection system which has at least two components;
   (c) a selective permeable vesicle having a surface bound ligand or ligand analog and a first component of said detection system therein;
   (d) a substance which modifies vesicle permeability in response to binding of surface-bound ligand or ligand analog and the binding partner; and
   (e) at least an additional component of said detection system which is reactive with said first component to produce a detectable response which is reduced when the vesicle is in the presence of the binding partner and vesicle modifying substance.

2. The composition of claim 1 wherein the vesicle is comprised of a lipid membrane.

3. The composition of claim 2 wherein the lipid membrane comprises a phospholipid.

4. The composition of claim 2 wherein the lipid membrane incorporates a sterol.

5. The composition of claim 2 wherein the lipid membrane includes an amphiphile to which the ligand or ligand analog is bound.

6. The composition of claim 1 wherein the vesicle is a biological cell membrane.

7. The composition of claim 1 wherein the first component of the detection system comprises a peroxidatively active substance and the additional component comprises a luminophore.

8. The composition of claim 7 wherein the peroxidatively active substance comprises peroxidase.

9. The composition of claim 7 further comprising an oxidant for the luminophore, which oxidant is a substrate for the peroxidatively active substance.

10. The composition of claim 9 wherein the oxidant is hydrogen peroxide.

11. The composition of claim 7 further comprising an enzymatic system effective to produce an oxidant for the luminophore.

12. The composition of claim 11 wherein the enzymatic system comprises glucose oxidase and glucose.

13. The composition of claim 1 wherein the detection system further comprises an energy transfer system.

14. The composition of claim 11 wherein the detection system comprises a luminophore and an energy transfer system including a fluor which absorbs light energy at the wavelength of the luminophore and fluoresces at a different wavelength.

15. The composition of claim 1 which comprises an additional substance which further diminishes the luminescence of said detection system upon the increase of vesicle permeability.

16. The composition of claim 15 wherein the additional substance is cyanide.

17. The composition of claim 1 wherein the ligand is a hapten or antigen and the binding partner is an antibody therefor.

18. The composition of claim 1 wherein the vesicle modifying substance is complement.

19. A composition for determining a ligand in a sample, which composition comprises:
   (a) antibody for said ligand;
   (b) complement;
   (c) a luminophore;
   (d) hydrogen peroxide; and
   (e) a liposome having a ligand or ligand analog on the surface thereof and peroxidase therein, which liposome exhibits a detectable signal that is reduced upon being bound with said antibody and complement.

20. A method for determining the presence and amount of a ligand in a sample, which method comprises the steps of:

(a) combining said sample and the composition of any of claims 1, 2, 7–10, 13 or 15–19 to form a reaction mixture;
(b) measuring the reduction of a detectable response of said reaction mixture; and
(c) comparing the detectable response conducted in the presence of said sample with the response conducted in the presence of a series of standard compositions containing known amounts of ligand as an indication of the presence and amount of ligand in the sample.

21. A composition for a detection system comprising:

(a) a selectively permeable vesicle;
(b) a first component of said detection system within said vesicle; and
(c) at least one additional component of said detection system which is reactive with said first component to produce a detectable response which is reduced by an increase in permeability of said vesicle.

22. The composition of claim 21 which comprises an additional substance which further diminishes the luminescence of said detection system upon the increase of vesicle permeability.

* * * * *